United States Patent [19]
Paltchkov et al.

[11] Patent Number: 5,831,090
[45] Date of Patent: Nov. 3, 1998

[54] PROCESS FOR THE PREPARATION OF PHOTOCHROMIC COMPOUNDS OF THE ANNELATED SPIRO[INDOLINE[2,3']BENZOXAZINE]TYPE

[75] Inventors: Victor A. Paltchkov; Nikolaï E. Chelepin; Vladimir I. Minkin; Nadezhda S. Trofimova; Oleg A. Zoubkov, all of Rostov on Don, Russian Federation

[73] Assignee: Essilor International - Compagnie Generale D'Optique, Charenton Cedex, France

[21] Appl. No.: 776,046
[22] PCT Filed: Jul. 22, 1994
[86] PCT No.: PCT/FR94/00918
§ 371 Date: Apr. 4, 1997
§ 102(e) Date: Apr. 4, 1997
[87] PCT Pub. No.: WO96/03368
PCT Pub. Date: Feb. 8, 1996
[51] Int. Cl.[6] .................. C07D 265/00; C07D 295/00
[52] U.S. Cl. ................................................. 544/71
[58] Field of Search ................................. 544/71

[56] References Cited

U.S. PATENT DOCUMENTS

| | | | |
|---|---|---|---|
| 4,634,767 | 1/1987 | Hoelscher et al. | 544/71 |
| 4,785,097 | 11/1988 | Kwak | 544/71 |
| 5,114,621 | 5/1992 | Guglielmetti et al. | 544/71 |
| 5,139,707 | 8/1992 | Giglielmetti et al. | 544/71 |
| 5,186,867 | 2/1993 | Castaldi et al. | 544/71 |
| 5,405,958 | 4/1995 | VanGemert | 544/71 |

OTHER PUBLICATIONS

Chemical Abstracts 111:39378q, Yamamoto et al. Jul. 1989.

*Primary Examiner*—Matthew V. Grumbling
*Attorney, Agent, or Firm*—Arnold, White & Durkee

[57] ABSTRACT

The present disclosure relates to a process for the preparation of photochromic compounds of the annelated spiro[indoline[2,3']benzoxazine] type comprising the reaction of a Fisher base (I) having a 2-alkylidene indoline structure with a condensed ortho-aminophenol compound (II) in the presence of an oxidizing agent. The Fisher base, condensed ortho-aminophenol and the oxidizing agent may be mixed together simultaneously in order to carry out the reaction. Alternatively, the oxidizing agent may be reacted with the Fisher base in a first step and condensed ortho-aminophenol may then be added to the reaction mixture thus obtained.

18 Claims, No Drawings

PROCESS FOR THE PREPARATION OF PHOTOCHROMIC COMPOUNDS OF THE ANNELATED SPIRO[INDOLINE[2,3']BENZOXAZINE]TYPE

This application claims benefit of PCT/FR94/00918, filed Jul. 22, 1994, under 35 U.S.C. §371.

The present invention relates to a novel process for the preparation of photochromic compounds of the annelated spiro[indoline[2,3']benzoxazine] type.

Photochromism is a well-known reversible phenomenon which is illustrated, for example, by a compound which changes color when it is exposed to light radiation some of which is in the UV region, in particular solar radiation, and which resumes its initial color when the exposure to light is interrupted.

Such compounds are used, for example, in the manufacture of lenses for protective sunglasses or in other applications which involve the need to vary the transparency of an article as a function of the surrounding light intensity. They may be applied to a transparent support or incorporated into a transparent polymerized organic material in combination with a very wide variety of polymer compositions.

A certain number of organic photochromic compounds containing an indolinospirooxazine group in their formula have already been proposed for such applications, particularly in the field of ophthalmic lenses.

Thus, U.S. Pat. Nos. 3,562,172 and 3,578,602 have disclosed the photochromic effect of certain compounds belonging to the family of indolinospironaphthoxazines, whereas U.S. Pat. No. 4,215,010 describes indolinospironaphthoxazines in which the naphthalene ring system is substituted with methoxy or ethoxy groups or a halogen atom. Analogous photochromic compounds containing a pyridobenzene ring system instead of the naphthalene ring system of the above compounds are described in U.S. Pat. No. 4,720,547, as well as in international application WO 87/00524.

However, the compounds described in this prior art do not fully satisfy all of the qualities expected thereof. If we consider more particularly the context of the application to sun-protective lenses, the photochromic material obtained, either from a solution of the photochromic compound or by incorporation of the latter into an organic polymer, must have a certain number of properties regarding the photochromic effect, in addition to its natural transparency and its compatibility with the materials commonly used for such lenses.

In particular:

When it is irradiated in its range of photo-sensitivity, the coloration must appear rapidly, preferably within a period of about a second, and its disappearance when the irradiation ceases must be just as rapid.

The material must be stable over time, both by itself and in its photochromism. Thus, the compound must be able to tolerate, within the material, a large number of coloration-decoloration cycles, throughout a period of use which may be several years.

The colorability must be good for reasonable contents of photochromic compound, and the absorption spectrum of the irradiated material must cover the entire visible spectrum as much as possible.

The photochromic effect should preferably be independent of the substrate containing the compound, and it should be exhibited over a wide temperature range, both at variable ambient temperatures and when it is heated under irradiation.

The coloration taken by the material under irradiation must also satisfy aesthetic concerns, by preserving a pleasant view of the environment for the wearer of ophthalmic spectacles or lenses made of such materials. From this point of view, blue colors, to which the compounds of the abovementioned prior art generally lead, should be avoided and green should be favored.

In the aim of satisfying these conditions, French patent applications 2,647,789 and 2,647,790 and European patent application EP-0,245,020 have already proposed photochromic compounds corresponding to the annelated spiro [indoline[2,3']benzoxazine] structure. These are spiro [indoline[2,3']benzoxazine] compounds in which the benzene ring of the benzoxazine part is ortho-fused to an aromatic or non-aromatic heterocyclic ring.

These compounds are obtained by a process including a condensation of a free Fischer base of the 2-alkylideneindoline type with an annelated 1-nitroso-2-phenol derivative.

According to a variant of this process, the Fischer base can also be prepared in situ from a corresponding indoleninium salt in the presence of a base such as piperidine or triethylamine.

The Applicant has discovered, unexpectedly, a novel process for the preparation of fused spiro[indoline[2,3'] benzoxazine] compounds which makes it possible to obtain higher yields of final product than in the prior processes defined above for the same final product.

The process of the invention also makes it possible to work under milder conditions than in the processes of the prior art.

The process of the invention is essentially characterized in that it includes the reaction of a Fischer base (I) of the 2-alkylideneindoline type with an annelated ortho-aminophenol compound (II) in the presence of an oxidizing agent.

According to a first variant, the Fischer base, the annelated ortho-aminophenol and the oxidizing agent are mixed together simultaneously in order to carry out the reaction.

According to a second variant of the process of the invention, the oxidizing agent is reacted with the Fischer base in a first step and the annelated ortho-aminophenol is then added to the reaction mixture thus obtained.

According to the different forms of the process of the invention, the Fischer base of the 2-alkylideneindoline type can also be formed in situ in the reaction medium from a precursor having the structure of an indoleninium halide corresponding to the said Fischer base, in the presence of a base such as piperidine or triethylamine.

The fused ortho-aminophenol compound can also be formed in situ from a precursor having the structure of an acidic addition salt of the said annelated ortho-aminophenol, in the presence of a base such as piperidine or triethylamine.

The condensation reaction of the Fischer base with the annelated ortho-aminophenol is preferably carried out in a solvent medium. The solvent used is preferably toluene or chloroform.

The oxidizing agents used according to the process of the invention are preferably chosen from oxides of a metalloid such as sulfur or selenium and oxides of a transition metal such as chromium.

Dimethyl sulfoxide, pyridinium chlorochromate or selenium dioxide are more preferably used. Dimethyl sulfoxide (DMSO) is particularly preferred insofar as it allows better yields of final product to be achieved.

The conditions for carrying out the process of the invention, in particular the choice of solvent, the temperature conditions and the use of certain additives for improving the yield of final product, vary as a function of the nature of the oxidizing agent.

When dimethyl sulfoxide (DMSO) is used, the process of the invention comprising the simultaneous mixing of the three reactants is preferably applied. Toluene is preferably used as solvent. A dehydrating agent such as magnesium sulfate or calcium chloride and/or a DMSO activator such as sodium hydrogen carbonate are more particularly used.

The condensation reaction temperature preferably ranges between 50° and 80° C.

When selenium dioxide is used, the process comprising two steps, namely oxidation of the Fischer base followed by addition of the annelated ortho-aminophenol to the reaction medium obtained, is more particularly applied. Toluene is preferably used as solvent. The first step of oxidation is preferably performed at room temperature in a solvent medium. The condensation reaction temperature preferably ranges between 50° and 100° C.

When pyridinium chlorochromate of formula Py $H^+ClCrO_3^-$ is used, the process of the invention in which the reactants are mixed together simultaneously is preferably applied. The solvent used is preferably chloroform. A basic reactant such as piperidine or triethylamine is preferably added to the reaction mixture after the step of condensation of the Fischer base in order to neutralize the excess oxidant.

The condensation reaction temperature is preferably about room temperature.

According to the present invention, spiro[indoline[2,3']benzoxazine] compounds are preferably synthesized, these compounds corresponding to the following formula:

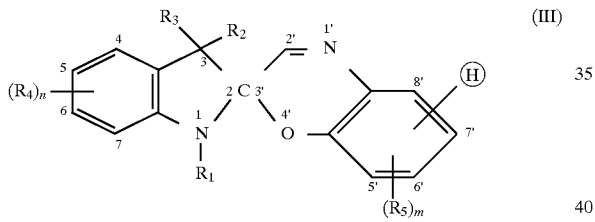

in which:
m is 1 or 2;
n ranges from 0 to 4;
$R_1$ represents:
  i) an alkyl group of 1 to 16 carbon atoms, such as methyl, ethyl, n-propyl, isopropyl or n-butyl;
  ii) an allyl or phenyl group, an arylalkyl group such as a benzyl group, a phenyl group mono- or disubstituted with substituents of the alkyl or alkoxy type of 1 to 6 carbon atoms, or halogen atoms such as chlorine;
  iii) an alicyclic group such as a cyclohexyl group which is optionally substituted;
  iv) an aliphatic hydrocarbon group containing one or more hetero atoms such as O, N or S in its chain, in particular an acid, ester or alcohol function;
$R_2$ and $R_3$ can, independently of each other, represent a $C_1$–$C_8$ alkyl group, a phenyl group, a phenyl group mono- or disubstituted with $C_1$–$C_4$ alkyl and/or $C_1$–$C_5$ alkoxy groups or may be combined to form a cyclic chain of 6 to 8 carbon atoms;
$R_4$ and $R_5$ can, independently of each other, represent:
  i) a hydrogen atom, an amine function NR'R", where R' and R" each independently represent a hydrogen atom, an alkyl, cycloalkyl or phenyl group or a substituted derivative thereof; R' and R" may combine to form a cycloalkyl which may be substituted and contain one or more hetero atoms;
  ii) a group R, OR, SR, COR or COOR, in which R represents a hydrogen atom, an alkyl group of 1 to 6 carbon atoms or an aryl or heteroaryl group;
  iii) a halogen atom, a $C_1$–$C_4$ monohaloalkyl group, the halogen being Cl or Br in particular, or a $C_1$–$C_4$ polyhaloalkyl group such as $CF_3$;
  iv) —$NO_2$, CN, SCN, it being possible for each of the substituents $R_4$ to be present on any one of the suitable carbon atoms in the indoline part of the photochromic compound, in positions 4, 5, 6 and 7, when the other is a hydrogen atom, whereas when n=2, it is preferable for the substituents to be present in positions 4 and 5, 5 and 6, 4 and 6 or 6 and 7.

If m=1, $R_5$ can also denote a 5',6'-fused benzene ring;

H denotes a 7',8'-fused benzene or naphthalene ring system or a 5- or 6-membered heterocycle containing 1 to 3 hetero atoms chosen from oxygen, sulfur and nitrogen, which may be substituted with one or more alkyl, alkoxy, amino, aryl or aralkyl groups or fused to an aromatic ring.

The heterocyclic rings more particularly preferred are chosen from a pyrimidine ring, a pyrazine ring, a furan ring optionally fused to an aromatic ring to form a benzofuran ring system, or a thiazole ring, these rings optionally being substituted.

The compounds of formula (III) are obtained by the process of the invention by reacting, in the presence of an oxidizing agent as defined above, a Fischer base of formula:

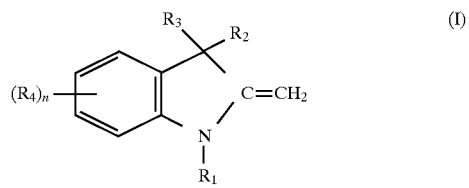

where $R_1$, $R_2$, $R_3$, $R_4$ and n have the same meanings indicated above, with an annelated ortho-aminophenol of the following formula:

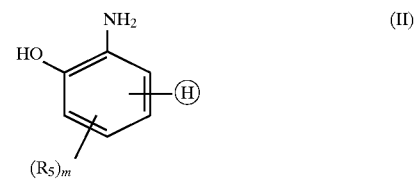

where $R_5$, m and H have the same meanings indicated above.

The preparation process allowing the compounds of formula (III) to be obtained may be represented by reaction scheme 1 below:

REACTION SCHEME A [sic]

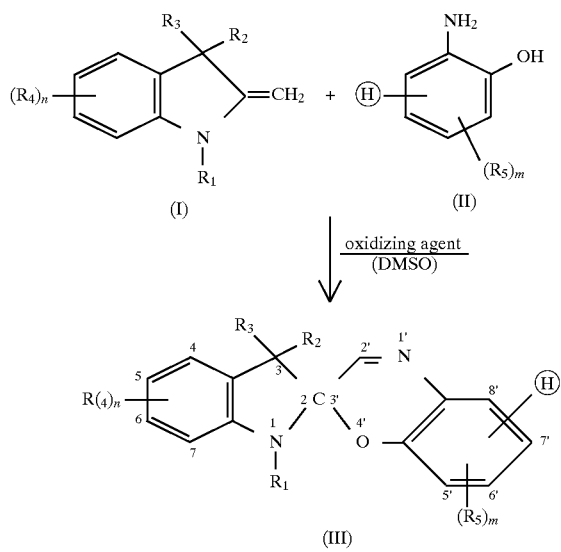

According to a variant of this preparation process, the Fischer base (I) is reacted with the oxidizing agent in a first step and the ortho-aminophenol (II) is added to the reaction mixture obtained in order to obtain the final spirooxazine (III).

This variant may be represented by reaction scheme 2 below, in which the formation of an intermediate product (IV) is envisaged.

This reaction scheme merely constitutes a possible explanation and should not lead to a limiting interpretation of the invention.

REACTION SCHEME 2

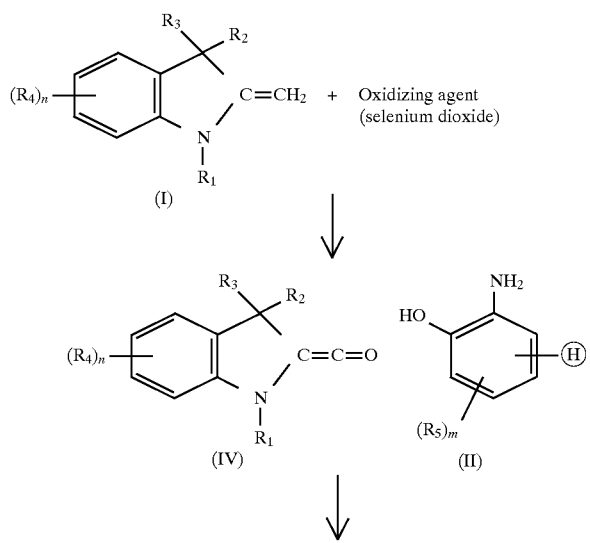

-continued
REACTION SCHEME 2

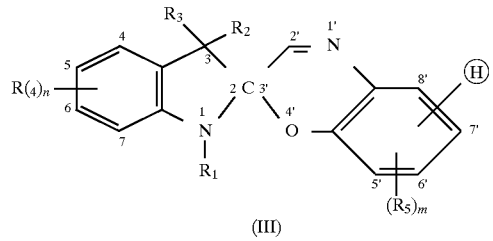

The compounds of formula (I) may be formed in situ in the reaction mixture in the presence of a base such as triethylamine or piperidine, from a precursor 5 having the structure:

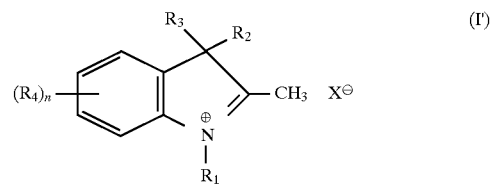

in which:

$R_1$, $R_2$, $R_3$, $R_4$ and n have the same meanings as in formula (III) indicated above; and X denotes a halogen atom, preferably iodine.

The compounds of formula (II) may be formed in situ in the reaction medium in the presence of a base such as triethylamine or piperidine, from precursors having the structure:

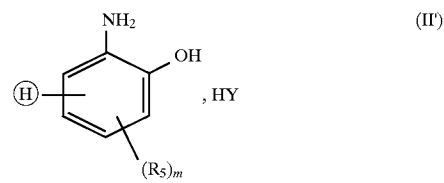

where $R_5$, m and H have the same meanings indicated above, and Y denotes $Cl^-$, $Br^-$ or $HSO_4^-$.

According to the present invention, compounds of formula:

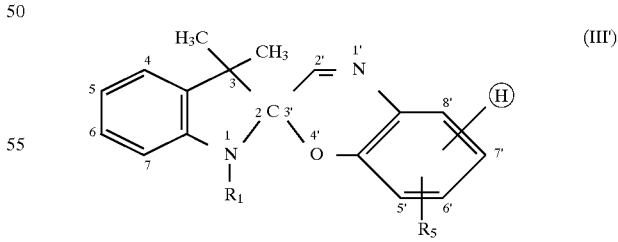

in which:

$R_1$ denotes a $C_1$–$C_8$ alkyl, benzyl or 3,4-dichlorobenzyl;

$R_5$ denotes a hydrogen atom or a 5',6'-fused benzene ring;

H has the same definition indicated in formula (III) above.

are more particularly synthesized with the processes as defined above.

7

The Fischer bases used have the formula:

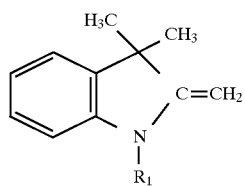

(IA)

Their precursors of the indoleninium halide type have the formula:

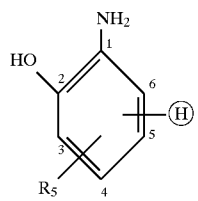

(IB)

in which $R_1$ has the same meanings indicated above and X denotes a halogen.

The annelated ortho-aminophenols used have the formula:

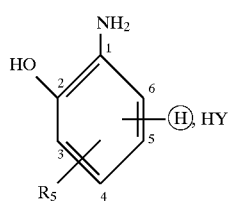

(IIA)

and their precursors in the form of addition salts of acids have the formula:

(IIB)

in which:

$R_5$ denotes a hydrogen atom or a 3,4-fused benzene ring;

H denotes a 5,6-fused benzene or naphthalene ring system or a heterocycle as defined in formula (III) above;

Y denotes $Cl^-$, $Br^-$ or $HSO_4^-$.

The examples which follow serve to illustrate the invention without, however, being limiting in nature.

8

EXAMPLES

Example 1

Syntheses of the compound 1,3,3-trimethylspiro [indoline-2,3'[3H]naphth[2,1-b][1,4]oxazine], of structure

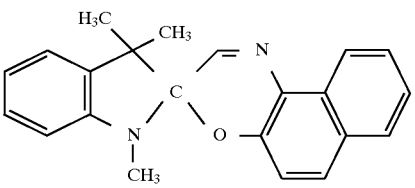

Synthesis A

The mixture composed of 0.173 g (1 mmol) of Fischer base, 0.159 g (1 mmol) of 1-amino-2-naphthol, 5 ml of toluene and 0.20 g (2.5 mmol) of dimethyl sulfoxide is heated for 6–7 hours at 50°–60° C. The reaction product is chromatographed with aluminum oxide. The product is crystallized from alcohol.

Yield: 0.24 g (72%)

Melting point: 125° C.

| Elemental analysis for $C_{22}H_{20}N_2O$: | | | |
|---|---|---|---|
| | % C | % H | % N |
| Calculated | 80.46 | 6.12 | 8.81 |
| Found | 80.53 | 6.25 | 8.77 |

The infrared and $^1H$ NMR spectra are in agreement with those of the expected product.

Synthesis B

The mixture composed of 0.173 g (1 mmol) of Fischer base, 0.215 g (1.1 mmol) of 1-amino-2-naphthol hydrochloride, 0.150 g (1.5 mmol) of triethylamine and 0.195 g (2.5 mmol) of dimethyl sulfoxide is heated for 6 hours at 50°–60° C. The reaction product is chromatographed with aluminum oxide. The product is crystallized from alcohol.

Yield: 0.19 g (60%)

Melting point: 125° C.

The infrared and $^1H$ NMR spectra are in agreement with those of the expected product.

Synthesis C

A solution of 0.173 g (1 mmol) of Fischer base in 10 ml of chloroform is added to the mixture of 0.24 g (1.1 mmol) of pyridinium chlorochromate and 0.159 g (1 mmol) of 1-amino-2-naphthol and the mixture is stirred for 2 hours at room temperature. 0.5 g of triethylamine is added. The solution is stirred and is filtered. The chloroform is evaporated off. The residue is diluted in toluene and is chromatographed on a column with aluminum oxide. The product is crystallized from alcohol.

Yield: 0.20 g (61%)

Melting point: 125° C.

| Elemental analysis for $C_{23}H_{20}N_2O$ | | | |
|---|---|---|---|
| | % C | % H | % N |
| Calculated | 80.46 | 6.15 | 8.51 |
| Found | 80.65 | 6.25 | 8.77 |

The infrared and $^1$H NMR spectra are in agreement with those of the expected product.

Synthesis D 0.16 g (1.44 mmol) of selenium dioxide is added to a solution of 0.173 g (1 mmol) of Fischer base in 6 ml of toluene. The reactant is stirred for 1–1.5 hours at room temperature. The toluene solution is separated from the residue after settling has taken place. 0.159 g (1 mmol) of 1-amino-2-naphthol is added thereto and the mixture is heated on a water bath at a temperature of 50°–100° C. The solution is filtered. The filtrate is evaporated, by lowering the pressure, to a small volume and is chromatographed on a column with aluminum oxide. The product is crystallized from alcohol.

Yield: 0.17 g (52%)

Melting point: 125° C.

| Elemental analysis for $C_{23}H_{20}N_2O$ | | | |
|---|---|---|---|
| | % C | % H | % N |
| Calculated | 80.46 | 6.15 | 8.52 |
| Found | 80.65 | 6.25 | 8.77 |

The infrared and $^1$H NMR spectra are in agreement with those of the expected product.

Example 2

Syntheses of the compound 1-propyl-3,3-dimethylspiro[indoline-2,3'[3H]naphth-[2,1-b][1,4]oxazine], of structure

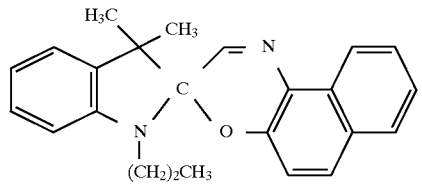

Synthesis A

The product is obtained according to method A described in Example 1.

Yield: 62%

Melting point: 123° C.

| Elemental analysis for $C_{24}H_{24}N_2O$ | | | |
|---|---|---|---|
| | % C | % H | % N |
| Calculated | 80.87 | 6.79 | 7.85 |
| Found | 81.00 | 6.92 | 7.94 |

The infrared and $^1$H NMR spectra are in agreement with those of the expected product.

Synthesis B

The product is obtained according to method C described in Example 1.

Yield: 47%

Melting point: 123° C.

| Elemental analysis for $C_{24}H_{24}N_2O$ | | | |
|---|---|---|---|
| | % C | % H | % N |
| Calculated | 80.87 | 6.79 | 7.85 |
| Found | 81.05 | 6.83 | 7.80 |

The infrared and $^1$H NMR spectra are in agreement with those of the expected product.

Synthesis C

The product is obtained according to method D described in Example 1.

Yield: 57%

Melting point: 123° C.

| Elemental analysis for $C_{24}H_{24}N_2O$ | | | |
|---|---|---|---|
| | % C | % H | % N |
| Calculated | 80.87 | 6.79 | 7.85 |
| Found | 81.05 | 6.83 | 7.80 |

The infrared and $^1$H NMR spectra are in agreement with those of the expected product.

Example 3

Syntheses of the compound 1-hexyl-3,3-dimethylspiro[indoline-2,3'[3H]naphth-[2,1-b][-1,4]oxazine], of structure Synthesis A The product is obtained according to method B described in Example 1.

Yield: 61%

Melting point: 90°–91° C.

| Elemental analysis for $C_{27}H_{30}N_2O$ | | | |
|---|---|---|---|
| | % C | % H | % N |
| Calculated | 81.37 | 7.60 | 7.02 |
| Found | 81.50 | 7.89 | 7.31 |

The infrared and $^1$H NMR spectra are in agreement with those of the expected product.

Synthesis B

The product is obtained according to method C described in Example 1.
Yield: 55%
Melting point: 90°–91° C.

| Elemental analysis for $C_{27}H_{30}N_2O$ | | | |
|---|---|---|---|
| | % C | % H | % N |
| Calculated | 81.37 | 7.60 | 7.02 |
| Found | 81.53 | 7.85 | 7.28 |

The infrared and $^1$H NMR spectra are in agreement with those of the expected product.

Synthesis C

The product is obtained according to method D described in Example 1.
Yield: 60%
Melting point: 90°–91° C.

| Elemental analysis for $C_{27}H_{30}N_2O$ | | | |
|---|---|---|---|
| | % C | % H | % N |
| Calculated | 81.37 | 7.60 | 7.02 |
| Found | 81.53 | 7.85 | 7.28 |

The infrared and $^1$H NMR spectra are in agreement with those of the expected product.

Example 4

Syntheses of the compound 1-benzyl-3,3-dimethylspiro[indolino-2,3'[3H]naphtho[2,1-b][1,4]oxazine, of structure

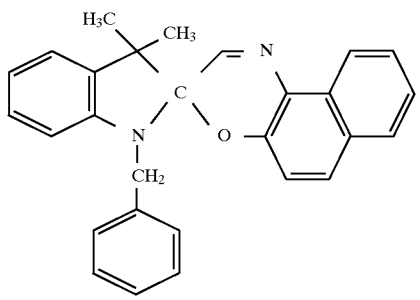

Synthesis A

The product is obtained according to method A described in Example 1.
Yield: 80%
Melting point: 192°–193° C.

| Elemental analysis for $C_{28}H_{24}N_2O$ | | | |
|---|---|---|---|
| | % C | % H | % N |
| Calculated | 83.14 | 5.99 | 6.92 |
| Found | 83.61 | 5.82 | 7.21 |

The infrared and $^1$H NMR spectra are in agreement with those of the expected product.

Synthesis B

The product is obtained according to method C described in Example 1.
Yield: 48%
Melting point: 192°–193° C.

| Elemental analysis for $C_{28}H_{24}N_2O$ | | | |
|---|---|---|---|
| | % C | % H | % N |
| Calculated | 83.14 | 5.99 | 6.92 |
| Found | 83.58 | 5.72 | 7.08 |

The infrared and $^1$H NMR spectra are in agreement with those of the expected product.

Synthesis C

The product is obtained according to method D described in Example 1.
Yield: 57%
Melting point: 192°–193° C.

| Elemental analysis for $C_{28}H_{24}N_2O$ | | | |
|---|---|---|---|
| | % C | % H | % N |
| Calculated | 83.14 | 5.99 | 6.92 |
| Found | 83.58 | 5.72 | 7.08 |

The infrared and $^1$H NMR spectra are in agreement with those of the expected product.

Example 5

Syntheses of the compound 1-[(3,4)-dichlorobenzyl]-3,3-dimethylspiro[indoline-2,3[3H]naphth-[2,1-b][1,4]oxazine, of structure

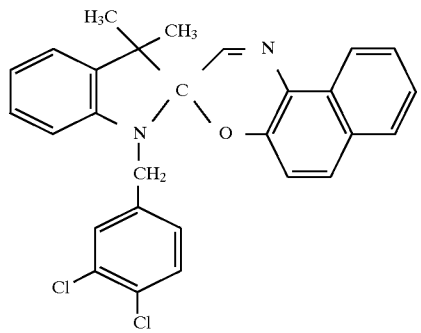

Synthesis A

The product is obtained according to method A described in Example 1.
Yield: 74%
Melting point: 177°–178° C.

| Elemental analysis for $C_{28}H_{22}Cl_2N_2O$ | | | |
|---|---|---|---|
| | % C | % H | % N |
| Calculated | 71.04 | 4.69 | 5.91 |
| Found | 71.43 | 4.85 | 6.08 |

The infrared and $^1$H NMR spectra are in agreement with those of the expected product.

Synthesis B
The product is obtained according to method C described in Example 1.
Yield: 55%
Melting point: 177°–178° C.

Elemental analysis for $C_{28}H_{22}Cl_2N_2O$

|  | % C | % H | % N |
|---|---|---|---|
| Calculated | 71.04 | 4.69 | 5.91 |
| Found | 71.52 | 4.92 | 6.01 |

The infrared and $^1$H NMR spectra are in agreement with those of the expected product.

Synthesis C
The product is obtained according to method D described in Example 1.
Yield: 60%
Melting point: 177°–178° C.

Elemental analysis for $C_{28}H_{22}Cl_2N_2O$

|  | % C | % H | % N |
|---|---|---|---|
| Calculated | 71.04 | 4.69 | 5.91 |
| Found | 71.54 | 4.92 | 6.01 |

The infrared and PMR spectra are in agreement with those of the expected product.

Example 6

Syntheses of 1,3,3-trimethylspiro[indoline-2,3'[3H]phenanthro[9,10-B][1,4]oxazine], of structure

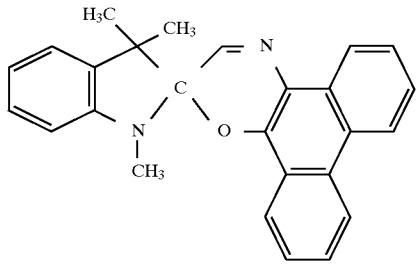

The mixture composed of 0.148 g (0.85 mmol) of Fischer base, 0.23 g (0.93 mmol) of 9-amino-10-phenanthrol hydrochloride, 5 ml of toluene, 0.17 g (2.1 mmol) of dimethyl sulfoxide and 0.13 g (1.27 mmol) of triethylamine is heated at 50°–60° C. for 6 hours. The mixture is chromatographed with aluminum oxide, taking out the blue-colored fraction. The product crystallizes from alcohol.
Yield: 0.22 g (63%)
Melting point: 193°–195° C.

Elemental analysis for $C_{26}H_{22}N_2O$

|  | % C | % H | % N |
|---|---|---|---|
| Calculated | 82.52 | 5.87 | 7.39 |
| Found | 82.68 | 5.82 | 7.48 |

The infrared and $^1$H NMR spectra are in agreement with those of the expected product.

Example 7

Syntheses of the compound 1,3,3-trimethylspiro[indoline-2,3'[3H]anthraceno[2,1-b][1,4]oxazine], of structure

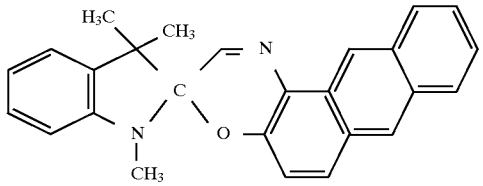

Synthesis A
The product is obtained according to method B of Example 1.
Yield: 52%
Melting point: 186° C.

Elemental analysis for $C_{26}H_{22}N_2O$

|  | % C | % H | % N |
|---|---|---|---|
| Calculated | 82.52 | 5.87 | 7.39 |
| Found | 82.68 | 5.77 | 7.52 |

The infrared and $^1$H NMR spectra are in agreement with those of the expected product.

Synthesis B
The product is obtained according to method C of Example 1.
Yield: 52%
Melting point: 186° C.

Elemental analysis for $C_{26}H_{22}N_2O$

|  | % C | % H | % N |
|---|---|---|---|
| Calculated | 82.52 | 5.87 | 7.39 |
| Found | 82.61 | 5.75 | 7.42 |

The infrared and $^1$H NMR spectra are in agreement with those of the expected product.

Synthesis C
The product is obtained according to method D of Example 1.
Yield: 52%
Melting point: 186° C.

Elemental analysis for $C_{26}H_{22}N_2O$

|  | % C | % H | % N |
|---|---|---|---|
| Calculated | 82.52 | 5.87 | 7.39 |
| Found | 82.61 | 5.75 | 7.42 |

The infrared and $^1$H NMR spectra are in agreement with those of the expected product.

COMPARISON BETWEEN TWO METHODS FOR THE PREPARATION OF 1,3,3-trimethylspiro[indoline-2,3'[3H]naphth[2,1-b][1,4]-oxazine]

I—Standard method
A solution of 2-methylene-1,3,3-trimethylindoline (0.173 g) (1.1 mmol) in 5 ml of trichloroethylene is added dropwise to a solution of 1-nitroso-2-naphthol (0.190 g) (1.1 mmol) in 10 ml of trichloroethylene. The mixture is maintained at reflux for 3 hours and is then evaporated and purified on a column of silica (100% dichloromethane). The expected spironaphthoxazine is recrystallized from ethanol.

Yield: 53%

Melting point: 125° C.

II—Method according to the invention 5 ml of toluene are added to a mixture of 2-methylene-1,3,3-trimethylindoline (0.173 g) (1.1 mmol), anhydrous calcium sulfate (0.2 g), dimethyl sulfoxide (0.117 g) (1.5 mmol), sodium hydrogen carbonate (0.25 g) and 1-amino-2-naphthol (0.175 g) (1.1 mmol) and the mixture is left stirring for 12 hours at 80° C. The reaction is monitored by TLC until a blue spot of $R_f$=0.3 on a neutral alumina plate (hexane/chloroform, 4:1) has disappeared. The mixture is filtered and washed with hot toluene (2 ml) and the filtrate is evaporated. The product is then purified on a column of silica (90 hexane/10 ethyl acetate).

Yield: 75%

Melting point: 125° C.

We claim:

1. Process for the preparation of photochromic compounds corresponding to the annelated spiro[indoline-[2,3'] benzoxazine] structure, comprising the condensation, in the presence of an oxidizing agent, of a Fischer base having a 2-alkylidene indoline structure onto a condensed ortho-aminophenol.

2. Process according to claim 1, wherein the Fischer base, the ortho-aminophenol and the oxidizing agent are mixed together simultaneously.

3. Process according to claim 1, wherein the oxidizing agent is reacted with the Fischer base in a first step and the condensed ortho-aminophenol is then added to the reaction mixture thus obtained.

4. Process according to claim 1, wherein the Fischer base having a alkylidene-indoline structure is formed in situ in the reaction medium from a corresponding indoleninium halide salt, in the presence of a base.

5. Process according to claim 1, wherein the condensed ortho-aminophenol is formed in situ in the reaction medium from an addition salt of the corresponding acid in the presence of a base.

6. Process according to claim 1, wherein it is carried out in a solvent medium.

7. Process according to claim 1, wherein it is carried out in a solvent chosen from toluene and chloroform.

8. Process according to claim 1, wherein the oxidizing agent is an oxide of a metalloid or an oxide of a transition metal.

9. Process according to claim 8, wherein the oxidizing agent is chosen from dimethyl sulfoxide, selenium dioxide and pyridinium chlorochromate.

10. Process according to claim 1, wherein the Fischer base, the condensed ortho-aminophenol and the dimethyl sulfoxide are mixed together simultaneously in toluene and the said mixture is heated to a temperature of 50°–80° C.

11. Process according to claim 10, wherein a dehydrating agent and/or a dimethyl sulfoxide-activating agent is added to the reaction medium.

12. Process according to claim 1, wherein the Fischer base is reacted with the selenium dioxide in toluene at room temperature and the condensed ortho-aminophenol is then added to the reaction medium, which is then heated to a temperature of 50°–100° C.

13. Process according to claim 1, wherein the Fischer base, the ortho-aminophenol and the pyridinium chlorochromate in chloroform are mixed together simultaneously at room temperature and at the end of the condensation reaction of the Fischer base with the condensed ortho-aminophenol, a basic reactant is then added to the final mixture.

14. Process according to claim 1, wherein compounds are synthesized corresponding to formula (III):

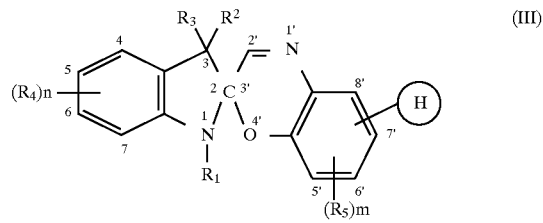

in which:

m is 1 or 2;

n ranges from 0 to 4;

$R_1$ represents:
  i) an alkyl group of 1 to 16 carbon atoms;
  ii) an allyl or phenyl group, an arylalkyl group mono- or disubstituted with substituents of the alkyl or alkoxy type of 1 to 6 carbon atoms, or halogen atoms such as chlorine;
  iii) an optionally substituted alicyclic group;
  iv) an aliphatic hydrocarbon group containing one or more hetero atoms chosen from O, N or S in its chain, and possibly an acid, ester or alcohol function;

$R_1$ and $R_3$ can, each independently of each other, represent a $C_1$–$C_8$ alkyl group, a phenyl group, a phenyl group mono- or disubstituted with $C_1$–$C_4$ alkyl and/or $C_1$–$C_5$ alkoxy groups or may be combined to form a cyclic chain of 6 to 8 carbon atoms;

$R_4$ and $R_5$ can, each independently of each other, represent:
  i) a hydrogen atom, amine function NR' R" where R' and R" each independently represent a hydrogen atom, an alkyl, cycloalkyl or phenyl group or a substituted derivative thereof; R' and R" may combine to form a cycloalkyl which may be substituted and contain one or more hetero atoms;
  ii) a group R, OR, SR, COR or COOR, in which R represents a hydrogen atom, an alkyl group of 1 to 6 carbon atoms or an aryl or heteroaryl group;
  iii) a halogen atom, a $C_1$–$C_4$ monohaloalkyl group, the halogen being Cl or Br in particular, or a $C_1$–$C_4$ polyhaloalkyl group such as $CF_3$;
  iv) —$NO_2$, CN, SCN, it being possible for each of the substituents $R_4$ to be present on any one of the suitable carbon atoms in the indoline part of the photochromic compound, in positions 4, 5, 6 and 7, when the other is a hydrogen atom, and when n=2, the substituents are present in positions 4 and 5, 5 and 6, 4 and 6 or 6 and 7;

if m=1, $R_5$ can also denote a 5',6'-fused benzene ring;

H denotes a 7',8'-fused benzene or naphthalene ring system or a 5- or 6-membered heterocycle containing 1 to 3 hetero atoms chosen from oxygen, sulfur and nitrogen, which may be substituted with one or more alkyl, alkoxy, amino, aryl or aralkyl groups or fused to an aromatic ring:

by reacting a Fischer base of formula (I):

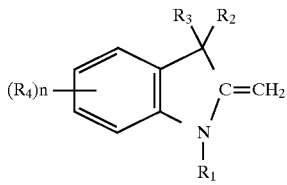 (I)

in which $R_1$, $R_2$, $R_3$, $R_4$ and n have the meanings indicated above, with a condensed ortho-aminophenol of formula (II) below:

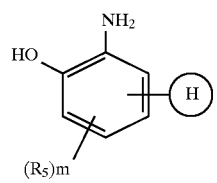 (II)

where $R_5$, H and m have the meanings indicated above, in the presence of the oxidizing agent.

15. Process according to claim 14, wherein the Fischer base of formula (I) is formed in situ from a precursor of formula (I'):

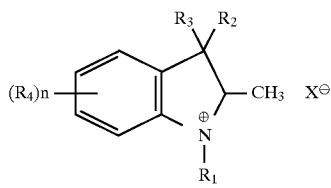 (I')

in which $R_1$, $R_2$, $R_3$, $R_4$ and n have the meanings indicated in claim 10, and X denotes a halogen atom, in the presence of a base.

16. Process according to claim 14, wherein the ortho-aminophenol of formula (II) is formed in situ from a precursor of formula (II'):

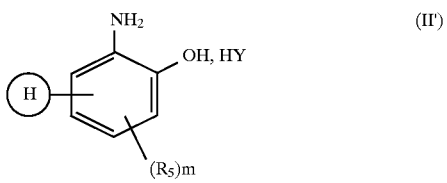 (II')

where $R_5$, H and m have the same meanings indicated above, and Y denotes $Cl^-$, $HSO_4^-$ or $Br^-$, in the presence of a base.

17. Process according to claim 1, wherein compounds of formula (III'):

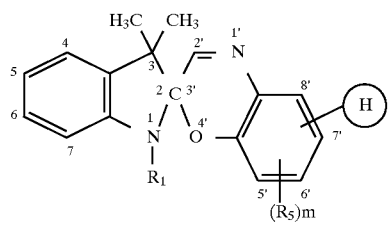 (III')

in which:

$R_1$ denotes a $C_1$–$C_8$ alkyl radical, a benzyl radical or a 3,4-dichlorobenzyl radical;

$R_5$ denotes a hydrogen atom or a 5',6'-fused benzene ring;

H denotes a 7',8'-fused benzene or naphthalene ring system or a 5- or 6-membered heterocycle containing 1 to 3 hetero atoms chosen from oxygen, sulfur and nitrogen, optionally substituted with one or more alkyl, alkoxy, amino, aryl or aralkyl groups or fused to an aromatic ring, are synthesized by reacting a Fischer base of formula (IA):

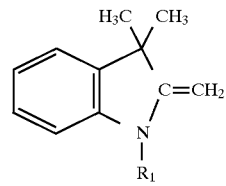 (IA)

with a condensed orth-aminophenol of formula (IIA)

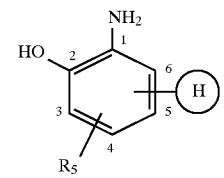 (IIA)

in the presence of the oxidizing agent, the radicals $R_1$, $R_5$ and H having the meanings indicated above, and $R_5$ is 3,4-fused when it denotes a benzene ring and H being 5,6-fused when it denotes a benzene or naphthalene ring system.

18. Process according to claim 17, wherein the Fischer base of formula (IA) is formed in situ from a precursor of formula (IB):

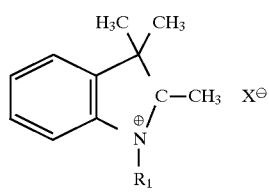 (IB)

or in that the ortho-aminophenol of formula (IIA) is formed in situ from a precursor of formula (IIB):

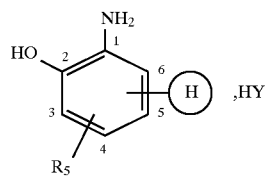 (IIB)

in which:

$R_1$, and $R_5$ have the same meanings indicated in claim 14;

X denotes a halogen; and

Y denotes $Cl^-$, $Br^-$ or $HSO_4^-$.

* * * * *